(12) United States Patent
Yamada et al.

(10) Patent No.: US 7,824,910 B2
(45) Date of Patent: *Nov. 2, 2010

(54) METHOD OF TRANSDUCING A PROTEIN INTO CELLS

(75) Inventors: Hidenori Yamada, Okayama (JP); Junichiro Futami, Nishinomiya (JP); Hidetaka Nakanishi, Suita (JP)

(73) Assignee: Nippon Shokubai Co., Ltd., Osaka-Shi, Osaka (JP)

( * ) Notice: Subject to any disclaimer, the term of this patent is extended or adjusted under 35 U.S.C. 154(b) by 502 days.

This patent is subject to a terminal disclaimer.

(21) Appl. No.: 10/306,165

(22) Filed: Nov. 29, 2002

(65) Prior Publication Data

US 2003/0138944 A1 Jul. 24, 2003

Related U.S. Application Data

(63) Continuation-in-part of application No. 10/156,888, filed on May 30, 2002, now abandoned.

(30) Foreign Application Priority Data

Nov. 29, 2001 (JP) .............................. 2001-363967
May 29, 2002 (JP) .............................. 2002-156197

(51) Int. Cl.
*C12N 5/00* (2006.01)

(52) U.S. Cl. .................... 435/325; 424/486; 424/193.1; 424/194.1; 514/2; 530/350; 530/300; 435/183

(58) Field of Classification Search .................. 435/325, 435/183; 424/486, 193.1, 194.1; 530/350, 530/300

See application file for complete search history.

(56) References Cited

U.S. PATENT DOCUMENTS

| 5,053,326 A | 10/1991 | Renz ............................... 435/6 |
| 6,696,274 B2 * | 2/2004 | Tchistiakova et al. ...... 435/69.1 |
| 2002/0115216 A1 * | 8/2002 | Steer et al. .................... 514/44 |
| 2009/0088679 A1 * | 4/2009 | Wood et al. ................... 604/20 |

FOREIGN PATENT DOCUMENTS

| CA | 2249058 | 3/1999 |
| WO | WO01/43778 A1 * | 6/2001 |

OTHER PUBLICATIONS

Junichiro Futami et al., "Preparation of Potent Cytotoxic Ribonucleases by Cationization: Enhanced Cellular Uptake and Decreased Interaction with Ribonuclease Inhibitor by Chemical Modification of Carboxyl Groups," Biochemistry, vol. 40, No. 25, 2001, pp. 7518-7524.
Shiro Futaki et al., "Arginine-Rich Peptides, An Abundant Source of Membrane-Permeable Peptides Having Potential as Carriers for Intracellular Protein Delivery," The Journal Of Biological Chemistry, vol. 276, No. 8, Feb. 23, 2001, pp. 5836-5840.
Steven Schwarze et al., "In Vivo Protein Transduction: Delivery of a Biologically Active Protein into the Mouse," Science, vol. 285, Sep. 3, 1999, pp. 1569-1572.
P. Grunwald et al., "Application of polyethylene imine as carrier material for enzyme immobilization," Naturwissenschaften, Berlin, DE vol. 68, No. 10, Oct. 1981, pp. 525-526.
M. Ogris et al., "The size of DNA/transferrin-PEI complexes is an important factor for gene expression in cultured cells," Gene Therapy, vol. 5, 1998, pp. 1425-1433.
Communication Pursuant to Article 96(2) EPC, mailed Dec. 22, 2006, for European Patent Application No. 02 258 244.9, filed Nov. 29, 2002.
Kircheis, R., et al., "Coupling of cell-binding ligands to polyethylenimine for targeted gene delivery," Gene Therapy, vol. 4, 1997, pp. 409-418.

* cited by examiner

*Primary Examiner*—Jon P Weber
*Assistant Examiner*—Susan Hanley
(74) *Attorney, Agent, or Firm*—Connolly Bove Lodge & Hutz LLP (57) ABSTRACT

The invention relates to a method for transducing a pharmaceutical protein or polypeptide that may be fluorescently labeled into a cell by forming a conjugate with a cationic polymer having cation values of more than 2 and no more than 250 and transducing the conjugate into the cell. The protein or peptide pharmaceutical agent is directly covalently bound to the cationic polymer or is covalently bound to the cationic polymer through a bifunctional crosslinking agent.

4 Claims, 11 Drawing Sheets
(7 of 11 Drawing Sheet(s) Filed in Color)

(a) observation views by fluorescence by transmitted beam (b)

by fluorescence by transmitted beam

METHOD OF TRANSDUCING A PROTEIN INTO CELLS

CROSS-REFERENCES TO RELATED APPLICATION

The application is a continuation-in-part of U.S. patent application Ser. No. 10/156,888, filed on May 30, 2002, now abandoned, and claims priority to Japanese Application No. 2002-156197, filed May 29, 2002 and Japanese Application No. 2001-363967, filed Nov. 29, 2001.

TECHNICAL FIELD

The present invention relates to a novel protein conjugate and a method for efficiently transducing a protein into cells using the conjugate.

BACKGROUND ART

Time signals of expression or modification of a protein engaged in proliferation, differentiation or development of various cells are now being clarified. When applying these findings to engineering fields such as regeneration medicine or tissue engineering, if it is possible to control the existence of a protein intended to function in cells at a designated amount for a designated period, it is expected to broaden various potentialities.

As a technique to enable a designated protein to function in cells, gene transfer is almost the only method available at present. When constant functioning of the designated protein in cells is desired, gene transfer is effective. However, when the designated protein is desired to transiently function in cells, it is preferable to transduce the protein itself into the cells.

Conventionally, as a method for transducing a protein itself into cells, because of the necessity of traverse through cell membranes, examples of methods to be used include a special method such as microinjection, and a method wherein a protein is encapsulated into a capsule-shaped material such as a liposome and the capsule shaped-material is fused with the cell membrane so as to transduce the content (protein etc.) of the capsule-shaped material into the cell. In addition, though the kinds of cells are limited, another method for transducing a protein into cells through a receptor-dependent route has come into practical use, wherein various receptors expressed on cell surfaces are targeted and ligands of these receptors are used as carriers.

The inventors have recently confirmed that apart from these routes, a highly cationic protein or a protein cationized by chemical modification was electrostatically adsorbed to a negatively charged cell surface, and accumulated in cells with high efficiency (Futami et al., Biochemistry, 40, 7518-7524, 2001). Likewise, recently it has been reported that a protein to which a highly basic TAT peptide derived from HIV (Schwarze et al., Science, 285, 1569-1572, 1999) or a cationic peptide (Futaki et al., J. Biol. Chem., 276, 5836-5840, 2001) such as Poly-Arg is added, can efficiently cross a cell membrane. Although in all the cases mentioned above, mechanisms have yet to be known in detail, a cell membrane crossing route mediated by the electrostatic interaction between a cationic protein and a cell surface is supposed.

However, a conventional protein cationization method requires modification of many amino acid side chains in a protein molecule, thereby deteriorating its function.

DISCLOSURE OF THE INVENTION

An object of the present invention is to provide a conjugate which enables a protein to be transduced into cells, and a method for transducing the protein into the cells using the conjugate with time and amount controllability and efficiency.

The present inventors have conducted studies to solve the above-described problems. As a result, the inventors have found that the problems can be solved by combining a polymer such as polyethyleneimine, which has a cation value, with a protein to cationize the protein, thereby accomplishing the present invention.

Namely, the present invention includes the following:

(1) A method for transducing a protein or peptide into a cell, comprising a step of transporting the protein or peptide into the cell by using a conjugate formed by binding the protein or peptide with a polymer having a cation value of more than 2 and no more than 30,000.

(2) The method according to (1) above wherein the polymer is a polymer having a polyalkylenepolyamine skeleton, a polyallylamine skeleton, a polyvinylamine skeleton, a poly(dialkylaminoalkyl(meth)acrylate) skeleton, a poly(meth)acrylic dialkylaminoalkylamide skeleton, a polyamidine skeleton, a polyvinylpyridine skeleton or polyvinylimidazole skeleton, or a salt thereof.

(3) The method according to (1) or (2) above wherein the polymer has a number average molecular weight within a range of from 100 to 1,000,000.

(4) The method according to any of (1) to (3) above wherein the conjugate is formed by binding the protein or peptide to the polymer via covalent bond.

(5) The method according to any of (1) to (4) above wherein the conjugate is formed by binding the protein or peptide to the polymer via an amide bond, disulfide bond or thioether bond.

(6) A method for transducing a protein or peptide into a cell, comprising a step of transporting the protein or peptide into the cell by using a conjugate formed by binding the protein or peptide with a polymer having a polyalkylenepolyamine skeleton.

(7) The method according to (6) above wherein the polymer is polyalkyleneimine.

(8) The method according to (6) or (7) above wherein the polymer is polyethyleneimine.

(9) The method according to any of (6) to (8) above wherein the polymer has a number average molecular weight within a range of from 100 to 1,000,000.

(10) The method according to any of (6) to (9) above wherein the polymer has a number average molecular weight within a range of from 100 to 100,000.

(11) The method according to any of (6) to (10) above wherein the conjugate is formed by binding the protein or peptide with the polymer via covalent bond.

(12) The method according to any of (6) to (11) above wherein the conjugate is formed by binding the protein or peptide with the polymer via an amide bond, disulfide bond or thioether bond.

(13) A conjugate formed by binding a protein or a peptide with a polymer having a cation value of more than 2 and no more than 30,000, and having a number average molecular weight within a range of from 100 to 1,000,000.

(14) The conjugate according to (13) above wherein the polymer is a polymer having a polyalkylenepolyamine skeleton, a polyallylamine skeleton, a polyvinylamine skeleton, a poly(dialkylaminoalkyl(meth)acrylate) skeleton, a poly(meth) acrylic dialkylaminoalkylamide skeleton, a polyamidine skeleton, a polyvinylpyridine skeleton or polyvinylimidazole skeleton, or a salt thereof.

(15) A method for delivering a pharmaceutical protein or peptide, wherein the method is carried out using a conjugate formed by binding the pharmaceutical protein or peptide with a polymer having a cation value of more than 2 and no more than 30,000 and having a number average molecular weight within a range of from 100 to 1,000,000.

Further, the present invention includes the following:

(1) A conjugate formed by binding a protein with a polyalkyleneimine;
(2) The conjugate according to (1) above wherein the polyalkyleneimine is polyethyleneimine;
(3) The conjugate according to (1) or (2) above wherein the polyalkyleneimine has a number average molecular weight within a range of from 100 to 100,000;
(4) The conjugate according to any one of (1) to (3) above wherein the protein is bound with the polyalkyleneimine via any one of an amide bond, disulfide bond, and thioether bond; and
(5) A method for transducing a protein into a cell, comprising a step of transporting the protein into the cell by using the conjugate according to any one of the above (1) to (4).

DETAILED DESCRIPTION OF THE INVENTION

The present invention will hereinafter be described in detail.

In this specification, "a protein or peptide" is defined as a compound produced by binding 2 or more amino acids with each other via a peptide bond. A protein or peptide to be used in the present invention is not limited, and any protein or peptide such as a peptide, an enzyme, an antibody, or a protein or a peptide which has other functions (physiological activity such as pharmacological action) and is effective as a medicine or a drug, can be used and the molecular weight thereof is preferably within a range of from 100 to 1,000,000. Incidentally, the term "protein" in this specification includes a conjugated protein formed by conjugation of a sugar chain, lipid and/or a phosphate group. Further, a structure of the protein may either be a native state or a denatured state.

A polymer to be used in the present invention which has a cationic group may be e.g. a polymer having a cation value of more than 2 and no more than 30,000. "Cation value" in this specification is defined as a value obtained by dividing the product of the amine value (mmol/g) and the number average molecular weight of the polymer by 1000. The cation value of the polymer to be used in the present invention is in general more than 2 and no more than 30,000, preferably more than 2 and no more than 20,000, more preferably more than 2 and no more than 2,500, in particular preferably more than 2 and no more than 250, and most preferably from 4 to 70. Incidentally, "amine value (mmol/g)" is an indicator of the total amine in a sample compound and it is represented as mmol number of amino groups that exist in 1g of the sample compound. The amine value of the sample compound may be measured according to a known method for quantitative analysis of amino group. Such quantitative analysis of amino group includes a method described in "Shin-jikkenn Kagaku Koza Vol. 13 Yuki-Kagaku-Kozo I" pp. 88-99 (MARUZEN Co., Ltd., edit. by the Chemical Society of Japan; pub. in Nov. 20, 1978) and colloidal titration method. Colloidal titration is described in "Colloidal titration method 1st Ed." (Nankodo Co., Ltd., edit. by R. Senju; pub. in Nov. 20, 1969). A suitable quantitative method should be chosen for accurate measurement of amine value, in consideration of a form and solubility of the sample compound, and contaminants in the sample. The amine value of the polymer to be used in the present invention is not particularly limited, but it is preferably within a range of from 1 to 30, more preferably 5 to 25.

Moreover, the polymer to be used in the present invention has a number average molecular weight, in general, within a range of from 100 to 1,000,000, preferably 100 to 100,000, more preferably 100 to 10,000, most preferably 200 to 3,000. In passing, for determining the number average molecular weight of the polymer, when the number average molecular weight of the polymer is 10,000 or less, ebullioscopic method is employed. When the number average molecular weight thereof exceeds 10,000, GPC is employed for accurate determination of molecular weight.

Examples of the polymer to be used in the present invention include a polymer having a polyalkylenepolyamine skeleton, a polyallylamine skeleton, a polyvinylamine skeleton, a poly (dialkylaminoalkyl(meth)acrylate) skeleton, a poly(meth) acrylic dialkylaminoalkylamide skeleton, a polyamidine skeleton, a polyvinylpyridine skeleton or polyvinylimidazole skeleton, and a co-polymer thereof. Further, a salt of these polymers e.g. primary, secondary, tertiary, or quarternary ammonium salt may be used as well. Additionally, those polymers, which are chemically altered or modified, may be used.

Specific examples of these polymers include polyalkylenepolyamine (e.g. polyalkyleneimine (polyethyleneimine, polypropyleneimine)), polyallylamine (e.g. polyallylamine, polydiallyldimethylammonium chloride), Hofmann decomposition product of polyacrylamide, polyvinylamine (e.g. a hydrolysate of polyvinylacetamide, a hydrolysate of polyvinylphthalimide, a hydrolysate of N-vinylformamide), dialkylaminoalkyl(meth)acrylamide (co)polymer (e.g. dimethylaminopropyl(meth)acrylamide (co)polymer), dialkylaminoalkyl(meth)acrylate (co)polymer (e.g. polymethacryloyloxyethyl trimethylammonium chloride), polyamidine, polyvinylpyridine, polyvinylimidazole, a dicyandiamide condensate, an epichlorohydrin.dialkylamine condensate (e.g. an epichlorohydrin.dimethylamine condensate), a dialkylamine.alkyldihalide condensate (e.g. a dimethylamine.ethylenedichloride condensate, polyvinylimidazoline, polyvinylbenzyl trimethylammonium chloride, carboxy methyl cellulose quarternary ammonium (quarternary ammonium CMC), glycolchitosan, cationized starch and the like.

Following is the theoretical amine values of typical polymers among the above-mentioned polymers. The theoretical amine values below are calculated by multiplying a reciprocal of molecular weight of a component monomer by 1,000. Generally, the amine value experimentally determined by the above-mentioned method is almost identical with the theoretical value within a range of measurement errors. The cation value of the polymer may be calculated on the basis of the amine value determined by the above-mentioned method. The amine value may be varied by changing a polymerization method, or copolymerizing with other components, or chemical modification of the polymer.

| | Amine value (mmol/g)* |
|---|---|
| polyethyleneimine | 23 |
| polyvinylamine | 23 |
| polyallylamine | 17 |
| polydiallyldimethylammonium chrolide | 6.2 |
| polymethacryloyloxyethyl trimethylammonium chloride | 4.8 |
| polymethacryloylaminopropyl trimethylammonium chloride | 4.5 |
| polyamidine | 6.0 |
| polyvinylbenzyl tri-methylammonium chloride | 6.3 |
| polyvinylpyridine | 10 |
| polyvinylimidazoline | 11 |
| epichlorohydrin•dimethylamine condensate | 7.2 |
| dimethylamin•ethylenedichloride condensate | 9.3 |

*theoretically maximum value

Hereinafter, a method for preparing the conjugate of the present invention will be described. When, for example, polyalkyleneimine is used as the polymer, the conjugate of the present invention is prepared as follows.

Examples of the polyalkyleneimine to be used in the present invention may be represented by the following general formula (I), and may be either linear or branched.

(I)

wherein each of $R^1$, $R^2$ and $R^3$ represents an alkylene group, X and Y are each an integer of 0 or more, and the sum of X and Y is 1 or more.)

The polyalkyleneimine is preferably a polyalkyleneimine wherein each of $R^1$, $R^2$ and $R^3$ in the above formula (I) is independently a $C_2$-$C_4$ alkylene group, and more preferably a polyethyleneimine wherein each of $R^1$, $R^2$ and $R^3$ in the above formula (I) is an ethylene group.

Hereinafter, the present invention is described in a case where polyethyleneimine is used, but the present invention is not limited thereto. Besides this, other polymers having a cation value of more than 2 and no more than 30,000 can be used in the same manner as below.

The polyethyleneimine (hereinafter referred to as "PEI") which is preferably used in the present invention, is represented by the following formula.

wherein X and Y are each an integer of 1 or more.

PEI is a water soluble polymer having a large positive charge density. In passing, PEI is used as a food additive such as a precipitant for fish sausage, and therefore safety in living bodies has been verified.

In the present invention, although either a PEI having a linear chain or a PEI having a branched structure with many branch chains can be used, a PEI having a branched structure represented by the following formula is preferable due to its high positive charge density. Additionally, in consideration of cell transduction efficiency, handleability etc., the PEI preferably has a number average molecular weight of 100 to 100,000, more preferably 100 to 10,000, and further more preferably 200 to 3,000. Such a low molecular weight PEI is particularly preferable.

A conjugate of the present invention is formed by binding the protein to the PEI. Herein the definition of the term "binding" is not particularly limited as long as it is a chemical bond, but it is preferably covalent bonding. The protein and the PEI may be directly bound without any intermediate therebetween. Alternatively, by use of a known bifunctional crosslinking reagent etc., they may be bound via an intermediate like a spacer. Although the number of PEI molecules to be bound to one molecule protein is not limited, the number is preferably 1 to 10, more preferably 1 to 3. Further, the number of binding sites for each PEI to the protein is preferably one. In the present invention, a conjugate having one PEI bound to one protein at one binding site is particularly preferable.

The binding between the protein and the PEI is not particularly limited, as long as it can bind the protein to the PEI by covalent bond. The binding is possible by various binding methods by use of known synthesis methods in the chemical field. Hereinafter the binding method of the protein to the PEI will be exemplified, but the binding method to be used in the present invention is not limited thereto.

When the protein and the PEI are bound via an amide bond, an amide bond can be formed between an amino group of the PIE and an asparatic acid residue, a glutamic acid residue, or a carboxyl group of C-terminal in the protein molecule by using an activator such as EDC (1-ethyl-3-(3-dimethylaminopropyl)-carbodiimide hydrochloride) and DCC (N,N-dicyclohexylcarbodiimide). An example case wherein EDC is used is schematically shown below.

When the protein and the PEI are bound via a disulfide bond, there can be formed a covalent bond including disulfide bond between an amino group of the PEI and a thiol group of a cysteine residue in the protein molecule by using a reagent such as SPDP (N-succinimidyl-3-(2-pyridyldithio)propionate). An example case wherein SPDP is used is schematically shown below.

Disulfide bond is reversible, and it dissociates under reducing conditions in the cytoplasm. Therefore, when the conjugate formed by disulfide bond is transduced into cells, the PEI is separated from the protein and thus the protein is expected to exhibit its function advantageously in cells.

Other examples for binding between the protein and PEI include a method for binding an amino group of the PEI to a lysine residue or an amino group of N-terminal in the protein molecule using 2-iminothiolane etc., and a method for forming a covalent bond including thioether bond between an amino group of the PEI and a thiol group of a cysteine residue in the protein molecule using GMBS (N-(4-maleimidebutyryloxy)succinimide) etc.

In addition to the binding method mentioned above, ether bond, ester bond, imide bond, carbon-carbon bond, amidine bond etc. may be used, and various binding methods can be employed with reference to the literature (e.g. "Tanpakushitu IV Kouzoukino-sokan (Protein IV Correlation between structure and its function)" by the Japanese Biochemical Society; 1st edition Mar. 20, 1991, published by Tokyo Kagaku Dozin).

Reference to the above-mentioned preparation methods and known synthetic means in the related technical fields also enables the preparation of a conjugate of the present invention even where a polymer other than polyalkyleneimine is used.

Further, the conjugate to be used in the present invention, if necessary, may be labeled. Although the labeling method is not particularly limited as long as it is a generally known method, preferable methods include fluorescent labeling, autoradiography, electron-dense material labeling, and insoluble pigment enzyme labeling. Particularly preferable is to fluorescent-label the conjugate by covalently binding the conjugate with the labeling compound.

Fluorescent substances to be used for fluorescent labeling is not particularly limited, and examples thereof include compounds having a fluorescent group such as pyrene, an anthraniloyl group, a dansyl group, fluorescein, rhodamine, or nitrobenzoxadiazol. Compounds having the above fluorescent groups are known (refer to e.g., Hiratsuka Toshiaki, "Tanpakushitu, Kakusan, Koso" Vol. 42, No. 7 (1997)), and these compounds can be introduced into protein molecules or peptides by conventional methods.

Next, a method for transducing a protein into cells using a conjugate of the present invention will be described, but the method of the present invention is not limited thereto.

To a medium containing cells to which the protein is to be transduced, the conjugates or a solution containing the conjugates of the present invention is added. Thereafter cells are cultivated under appropriate conditions including culture temperature, culture period etc., and thereby the conjugates of the present invention are accumulated in the cells. With the passage of time, the amount of the conjugates accumulated in the cells is increased. According to the method of the present invention, the amount of protein to be transduced into the cells can easily be controlled by changing the absolute amount, concentration, period for adding of the conjugates, and the like. Incidentally, it is assumed that the conjugates of the present invention can be accumulated in the cells by a mechanism attributable to electrostatic interaction between the positively charged conjugates and a negatively charged cell surface. Thus, for accumulating the conjugates in the cells in the medium, it is preferable to conduct the above process in the absence of anionic polymers such as heparin and nucleic acid. Further, the solution containing the conjugates of the present invention is inoculated directly on a living body by a method e.g. oral administration, intravenous administration, injection to an affected area, and dermal application, thus allowing conjugates to be accumulated in the cells of the living body.

In view of the foregoing, the method of transducing a protein or peptide into cells according to the present invention wherein the protein or peptide is transduced using a conjugate which is formed by binding the protein or peptide with a polymer having a cation value of more than 2 and no more than 30,000, and the conjugate used therefor may be employed for applications of in vivo function analysis of proteins or peptides, and further for medical products, medicines, reagents, support for drug development, and regenerative medicine. Preferred embodiments include, for example, a conjugate which is formed by binding a protein or peptide as a pharmaceutical agent (e.g., enzymes, antibodies, and hormones) having physiological activity (e.g. pharmacological action) with a cationized polymer can be used as a medicine. For such a medicine, the cationized polymer works as a carrier to efficiently deliver the pharmaceutical protein or peptide into cells, and thereby making the medicine very useful.

This specification includes part or all of the contents as disclosed in the specification and/or drawings of Japanese Patent Application Nos. 2001-363967 and 2002-156197, which are priority documents of the present application.

BRIEF DESCRIPTION OF THE DRAWINGS

This patent or application file contains at least one drawing executed in color. Copies of this patent or patent application publication with color drawing(s) will be provided by the Office upon request and payment of the necessary fee.

BEST MODE FOR EMBODYING THE INVENTION

The present invention will hereinafter be explained more in detail by way of Examples and Reference examples, but the scope of the present invention is limited in no way by the following Examples.

In the Examples, a number average molecular weight is determined by ebullioscopic method, and the amine values are determined by acid neutralization titration. A cation value is calculated using a number average molecular weight and the amine value determined as mentioned above.

In the following Examples, PEIs (Nippon Shokubai: tradename "EPOMIN") having a number average molecular weight of 250, 600, 1000, 1200, and 1800 were used and they are described as PEI250, PEI600, PEI000, PEI1200, and PEI1800, respectively.

EXAMPLE 1

Synthesis of RNaseA-PEI Conjugate

RNaseA, which is an enzyme that induces cell proliferation inhibition associated with protein synthesis inhibition with transduction into cells, was used as a protein.

Figure 1:
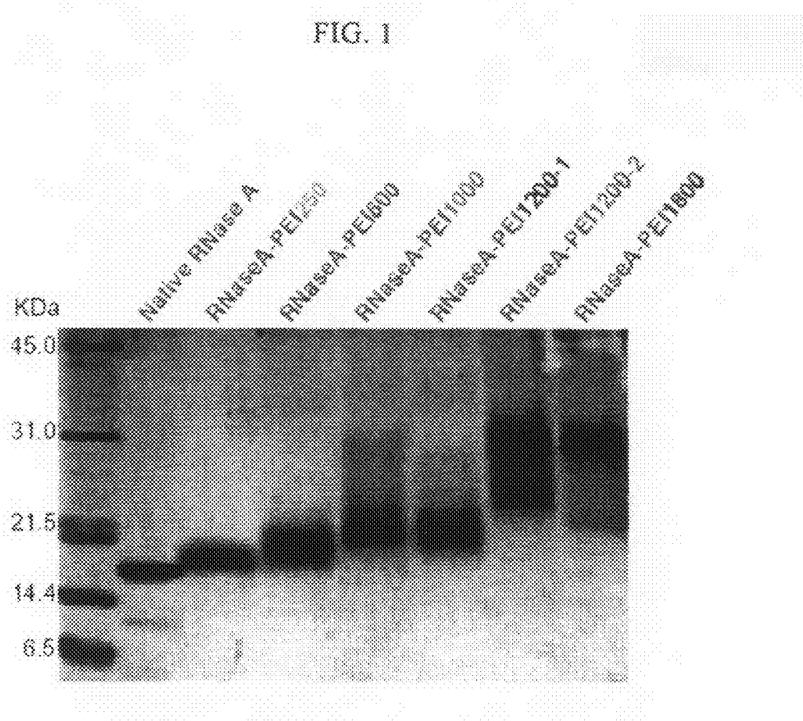
FIG. 1 is electropherogram of RNaseA-PEI conjugates of the present invention and native RNaseA.

15 mg of RNaseA was dissolved in 1.5 ml of 60 mg/ml PEI aqueous solution (pH was adjusted to 5 with hydrochloric acid). 2.5 mg of EDC was added thereto, and the obtained solution was stirred for 16 hours at room temperature. After the reaction was completed, the reaction solution was dialyzed against water and finally purified by cationic ion exchange chromatography (CM-TOYOPEARL 650M) to give RNaseA-PEI conjugate (1 to 2 molecules of PEIs were bound per 1 molecule of RNaseA). About 1.5 μg of the obtained RNaseA-PEI conjugate was analyzed with 15% SDS-PAGE. The results are shown in FIG. 1.

Evaluation of Protein Function in RNaseA-PEI Conjugate

The hydrolytic rate of RNA catalyzed by RNase was measured using yeast RNA as a substrate, and the RNaseA-PEI conjugate was compared with native RNaseA in terms of enzyme activity. The relative activity of RNaseA-PEI conjugate to native RNaseA is shown in Table 1. In addition, the amine value and cation value of each PEI is also shown in Table 1. Here, RNaseA-PEI1200-1 and RNaseA-PEI1200-2 represent an RNaseA-PEI conjugate wherein about 1 and 2 molecules of PEI1200s were bound per 1 molecule of RNaseA, respectively. According to the results of Table 1, the conjugate of the present invention exhibited remarkably high enzyme activity in comparison with RNaseA-ethylenediamine prepared by a conventional method, and it was clear that the reduction of inherent function possessed by RNaseA was small.

TABLE 1

| Conjugate | Relative activity (%) |
|---|---|
| native RNaseA | 100 |
| RNaseA-PEI250 | 20.4 |
| RNaseA-PEI600 | 21.9 |
| RNaseA-PEI1000 | 28.0 |

TABLE 1-continued

| Conjugate | Relative activity (%) |
|---|---|
| RNaseA-PEI1200-1 | 27.2 |
| RNaseA-PEI1200-2 | 8.9 |
| RNaseA-PEI1800 | 27.2 |
| RNaseA-ethylenediamine[1] | 1.6 |

[1] about 8 ethylenediamines combined with 1 RNaseA

| | Number average molecular weight (Mn) | Amine value (mmol/g) Found (Calcd.) | Cation value Amine value × Mn)/1000 Found (Calcd.) |
|---|---|---|---|
| Etyhlenediamine | 60 | — (33) | — (2.0) |
| PEI-100 | 100 | — (23) | — (2.3) |
| PEI-200 | 200 | — (23) | — (4.7) |
| PEI-250 | 250 | 21 (23) | 5.3 (5.8) |
| PEI-300 | 300 | 21 (23) | 6.3 (7.0) |
| PEI-600 | 600 | 20 (23) | 12 (14) |
| PEI-1000 | 1000 | 19 (23) | 19 (23) |
| PEI-1200 | 1200 | 19 (23) | 23 (28) |
| PEI-1800 | 1800 | 18 (23) | 32 (42) |
| PEI-3000 | 3000 | — (23) | — (70) |
| PEI-10000 | 10000 | 18 (23) | 180 (233) |
| PEI-20000 | 20000 | 18 (23) | 360 (460) |
| PEI-100000 | 100000 | — (23) | — (2330) |
| PEI-1000000 | 1000000 | — (23) | — (23300) |

Transduction of RNaseA-PEI Conjugate into Cells

Figure 2:
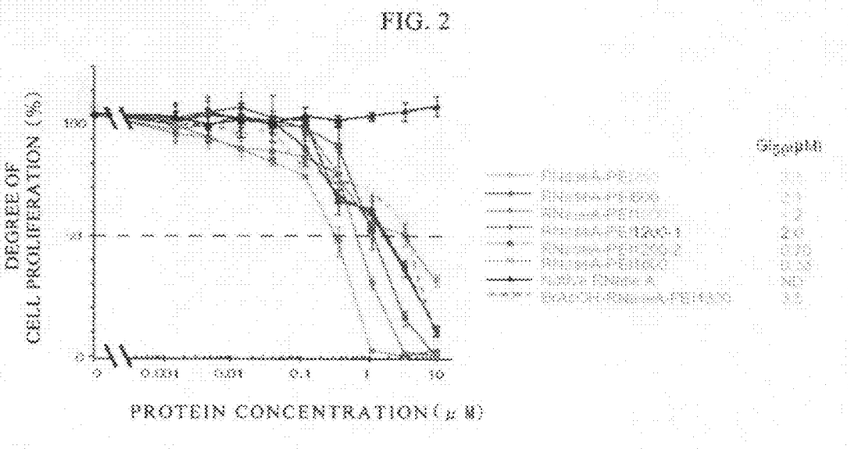
FIG. 2 is a graph showing the accumulation of RNaseA-PEI conjugates of the present invention into 3T3/SV40 cells and cell proliferation inhibition activity.

With respect to the above conjugates, cell proliferation inhibition activity against 3T3/SV40 cells was evaluated. In the cell proliferation inhibition activity experiment, a 96 well-plate was used. One thousand five hundred 3T3/SV40 cells per well were cultivated on DMEM+10% FBS medium for 12 hours. To the culture supernatant thereof, native RNaseA and RNaseA-PEI conjugates were added at various concentrations for each, and 3 days. Then, the cell proliferation degree was evaluated by MTT method. The results thereof are shown in FIG. 2. Native RNaseA was not accumulated in the cells and did not exhibit a significant inhibition of cell proliferation. In contrast, the conjugates of the present invention were effectively transduced into cells and it was confirmed that the conjugates exhibited inhibition of cell proliferation in proportion to the positive charge amount of the transduced PEIs.

EXAMPLE 2

Synthesis of eGFP-PEI Conjugate

Enhanced Green Fluorescent Protein (eGFP available from CLONTECH) was used as a protein, thus allowing protein transduction into cells to be easily observed by fluorescence. The eGFP containing His tag at the amino terminal was expressed in *Escherichia coli* as a recombinant protein and purified.

Figure 3:
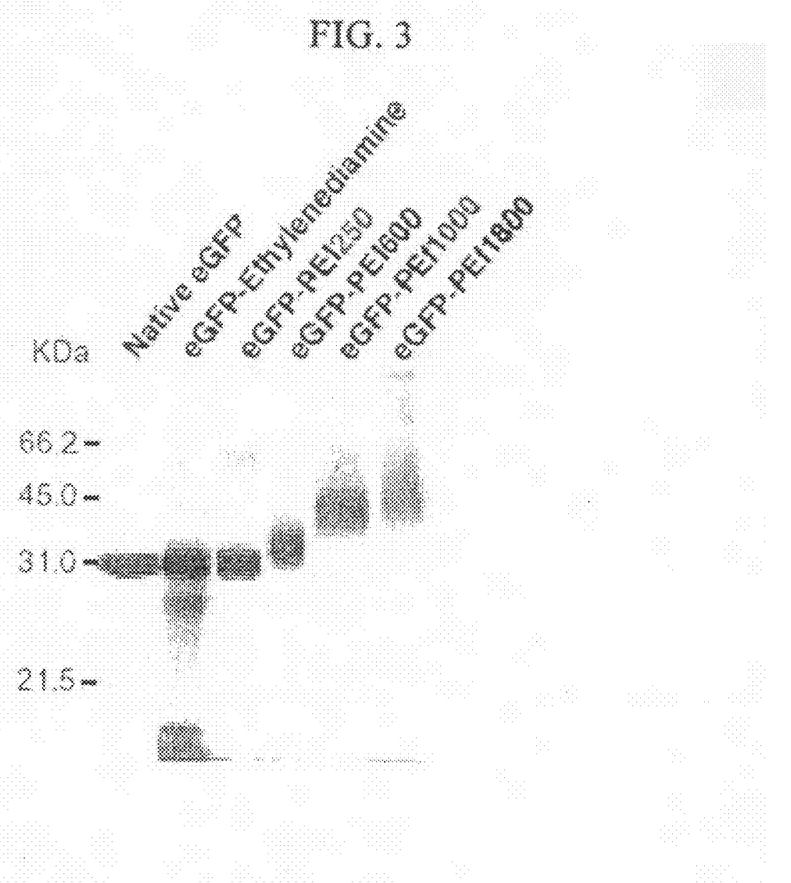
FIG. 3 is electropherogram of eGFP-PEI conjugates of the present invention, native eGFP and eGFP-ethylenediamine conjugate.

3 mg of eGFP was dissolved in 4.5 ml of 60 mg/ml PEI aqueous solution (adjusted to pH 5 with HCl). 10 mg of EDC was added thereto and the resultant solution was stirred for 30 seconds by a vortex mixer. Thereafter it was incubated at room temperature for 16 hours. The reaction solution was dialyzed against water, and finally purified by HiTrap(Ni+) chelate column to give an eGFP-PEI conjugate. The obtained eGFP-PEI conjugates were analyzed with 15% SDS-PAGE. The results are shown in FIG. 3.

Evaluation on Function of eGFP-PEI Conjugate

Figure 4:
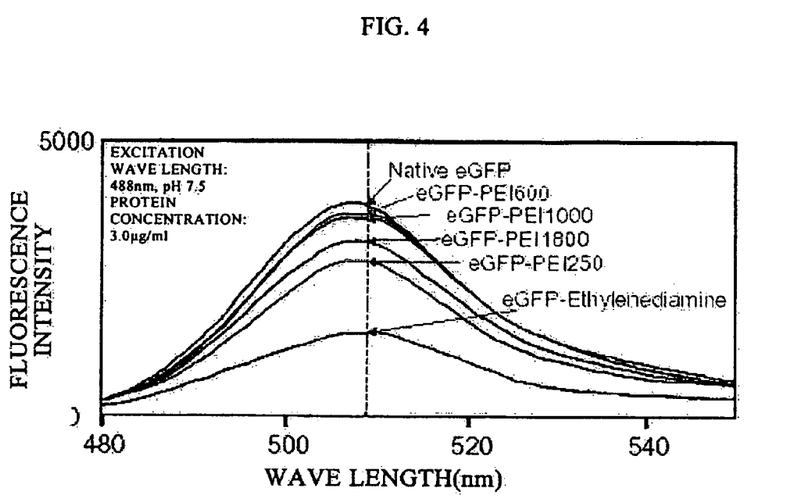
FIG. 4 is a graph showing comparison of fluorescence intensity among eGFP-PEI conjugates of the present invention, native eGFP and eGFP-ethylenediamine conjugate.

Native eGFP and the e-GFP-PEI conjugates of the present invention were compared with eGFP-thylenediamine conjugate in terms of fluorescence intensity. Results are shown in FIG. 4. As can be shown in FIG. 4, in comparison with the conjugate multi-modified with ethylenediamine by a conventional method, the eGFP modified with about 1 PEI retained as high a fluorescence intensity as the native eGFP, and it was indicated that PEI modification does not exert a large influence on eGFP function.

Transduction of eGFP-PEI Conjugates into Cells

Figure 5:
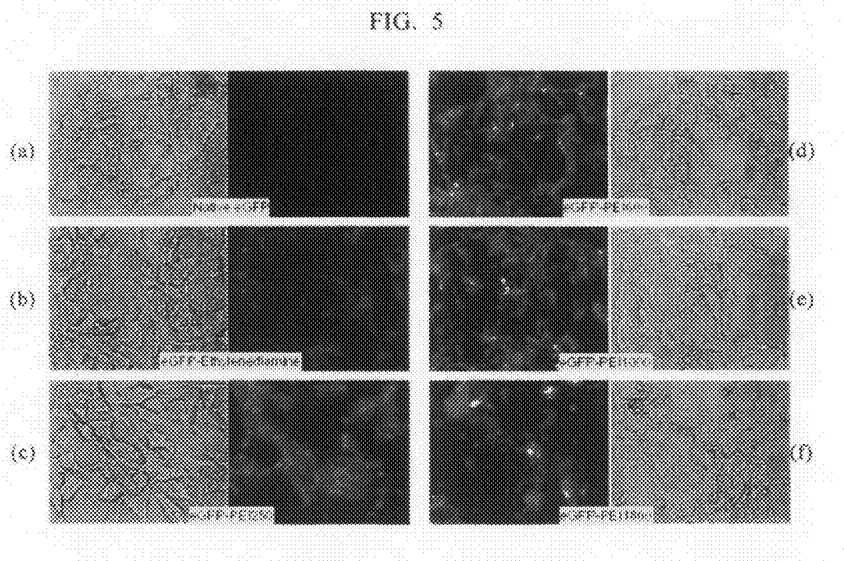
FIGS. 5(a)-(f) are observation views by fluorescence which show the accumulation of eGFP-PEI conjugates of the present invention, native eGFP and eGFP-ethylenediamine conjugate into Balb/c3T3 A31K cells.

Balb/c3T3 A31K cells were cultivated on DMEM+10% FBS, 100 nM of eGFP-PEI conjugates (3 μg/ml) were added to the culture supernatant thereof. After 8 hours, accumulation of eGFP was observed by fluorescence. For comparison, tests on native eGFP and eGFP-ethylenediamine conjugate were carried out in the same manner as above. Results are shown in FIG. 5(*a*)-(*f*). As can be shown in FIG. 5, there was almost no accumulation in the cells for either native eGFP (FIG. 5(*a*)) or eGFP-ethylenediamine (FIG. 5(*b*)) conjugate, whereas the eGFP-PEI conjugates (FIG. 5(*c*)-(*f*)) were effectively accumulated in the cells. Incidentally, the fluorescence observation was conducted on live cells, and fixation etc. was not carried out.

EXAMPLE 3

Synthesis of T7 RNA Polymerase-PEI1200 Conjugate

T7 RNA Pol. has a molecular weight of 100 kDa and 2 cystein residues are exposed on a molecular surface. A recombinant T7 RNA Pol. was expressed in *E. coli*. The obtained T7 RNA Pol. was purified, and a 4.62 mg/ml (46.8 μM) aqueous solution thereof was prepared. 0.107 ml of 100 mg/ml PEI1200 aqueous solution (adjusted to pH 8 with hydrochloric acid) and 1.4 mg/0.1 ml of SPDP ethanol solution were further mixed together (molar ratio, PEI1200:SPDP=2:1). This mixture solution was mixed with T7 RNA Pol. aqueous solution so that the molar ratio of SPDP to T7 RNA Pol. became 10:1, and then the obtained mixture was stirred for 16 hours at room temperature. After the reaction, gel filtration was conducted for purification, and consequently T7 RNA Pol.-PEI1200 conjugate wherein 2 molecules of PEI1200 were bound per 1 molecule of T7 RNA Pol. was obtained.

Figure 6:
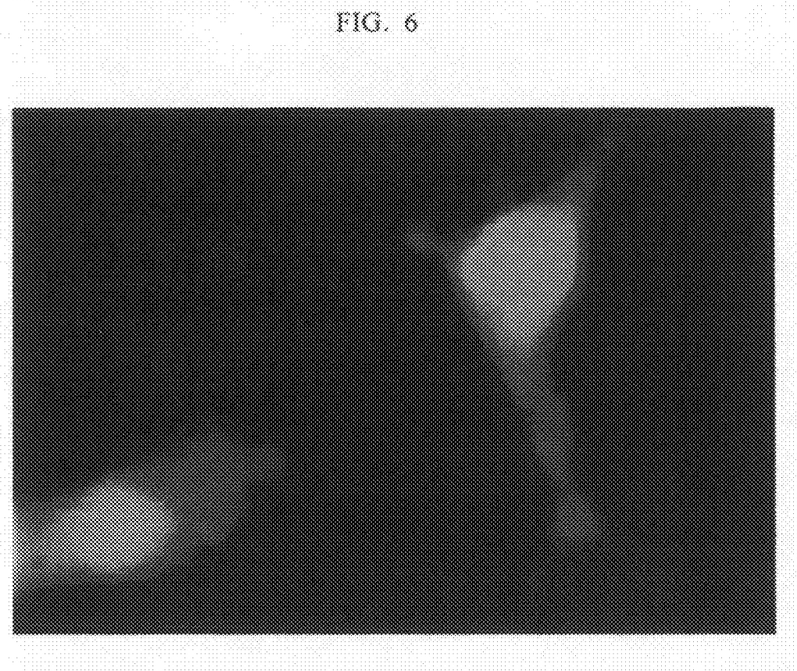
FIG. 6 is an observation view by fluorescence which shows expression of a reporter gene (eGFP) in T7-eGFP/COS-7 cells.

Expression of a Reporter Gene (eGFP) by Transducing T7 RNA Pol.-PEI1200 into Cells A plasmid DNA having an eGFP gene connected downstream of a T7 promoter was introduced into a COS-7 cell by electroporation for preparing a T7-eGFP/COS-7 cell. 1 μM of T7 RNA Pol.-PEI1200 was added to the culture solution of T7-eGFP/COS-7 cells (DMEM+10% FBS medium), and the mixture was cultivated for 1 day at room temperature. After cultivation, eGFP expression was observed by fluorescence. FIG. 6 shows an observation view thereof. In contrast, without the addition of T7 RNA Pol.-PEI1200, it was confirmed that the eGFP gene was not expressed.

EXAMPLE 4

Figure 7:
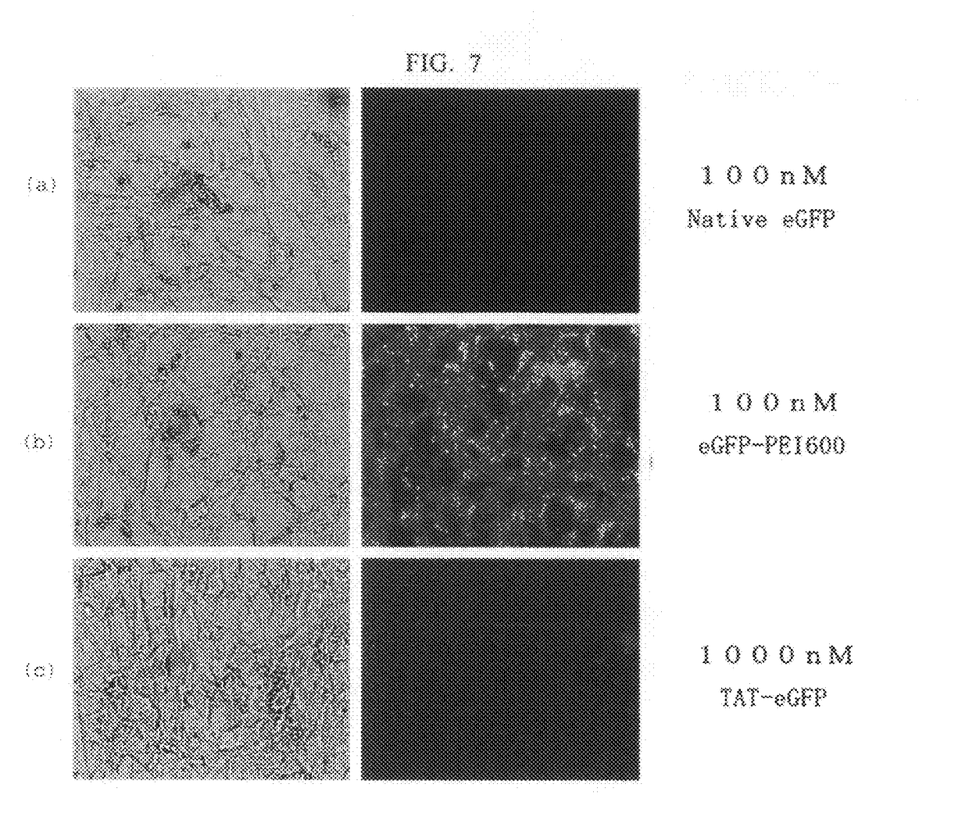
FIGS. 7(a)-(c) are observation views showing comparison of transduction efficiency of native eGFP, eGFP-PEI600 conjugate, and TAT-eGFP fusion protein into Balb/c3T3 cells.

Comparison of Cell Transduction Efficiency by eGFP-PEI600 Conjugate and TAT-eGFP Fusion Protein 100 nM of the eGFP-PEI600 conjugate synthesized in accordance with Example 2 was added to 10% FBS+DMEM medium containing Balb/c3T3 cells, and cultivated for 6 hours at 37° C. After cultivation, the accumulation of eGFP in the cells was observed by fluorescence. Further, as a comparison, a fusion protein having TAT peptide added to the amino terminal side of eGFP was expressed in *E. coli* as a recombinant protein and purified. Then 1000 nM of the TAT-eGFP fusion protein was added to DMEM+10% FBS medium containing Balb/c3T3 cells, and cultivated for 6 hours at 37° C. After cultivation, accumulation of eGFP in cells was observed by fluorescence. The TAT peptide is a peptide having an amino acid sequence of GRKKRRQRRRG, and it is reported that the protein can be accumulated easily in the cells by conjugating it with a protein. The results are shown in FIG. 7(*a*)-(*c*). According to the results shown in FIG. 7, when the TAT-eGFP fusion protein was used, almost no protein was accumulated in the cells (FIG. 7(*c*)). In contrast, when the eGFP-PEI600 conjugate of the present invention was used, even at a concentration of one-tenth of TAT-eGFP fusion protein, the protein was accumulated in the cells with high efficiency (FIG. 7(*b*)).

EXAMPLE 5

Synthesis of a RNaseA-PEI600 Conjugate Using 2-Iminothiolane 10 mg (0.73 µmol) of RNaseA was dissolved in 500 µl of 0.1 M phosphate buffer solution (pH 8). 0.5 mg (3.6 µmol) of 2-iminothiolane was added thereto and the mixture solution was stirred for 15 minutes at room temperature. Then, 10 mg (36 µmol) of $BrCH_2CONHNHCOCH_2Br$ was added, and dispersed with ultrasonic. Then the obtained solution was stirred for 1 hour at room temperature. After the reaction was completed, the reaction solution was centrifuged. The supernatant thereof was mixed with 0.5 ml (83 µmol) of 10% PEI solution (adjusted to pH 8), and stirred for 1 hour at room temperature. After the reaction was completed, the reaction solution was dialyzed against water to give a RNaseA-PEI600 conjugate.

The thus obtained conjugate was tested in the same manner as in Example 1 with respect to cell proliferation inhibition against 3T3/SV40 cells. It was confirmed that the RNaseA-PEI600 conjugate obtained by using 2-iminothiolane as well as the RNaseA-PEI600 conjugate obtained by using EDC were both effectively accumulated in the cells and exhibited inhibition of cell proliferation.

EXAMPLE 6

Transduction of IgG-PEI-FITC into Cells

Synthesis of FITC-IgG-PEI600 Conjugates 10 mg of IgG (derived from goat, SIGMA) was dissolved into 0.5 ml of 0.1 M sodium carbonate aqueous solution (pH 9.3). 3.0 mg of FITC (I type, Dojindo Corporate) was dissolved into 1 ml of DMF, and 30 µl of this FITC dissolved solution was added to the IgG solution. After 2 hours of reaction at room temperature, the solution was purified with gel-filtration, thereby obtaining FITC-modified IgG. 3 mg of this FITC-modified IgG was dissolved into 1 ml of PEI600 aqueous solution (adjusted to pH 5 with hydrochloric acid) having a concentration of 60 mg/ml. Next, 3.0 mg of EDC was added thereto and allowed to react with each other for 4 hours at room temperature. Then, the resultant solution was dialyzed against water and PBS solution, thereby obtaining FITC-IgG-PEI600 conjugates.

Transduction of FITC-IgG-PEI600 into Cells

Figure 8:
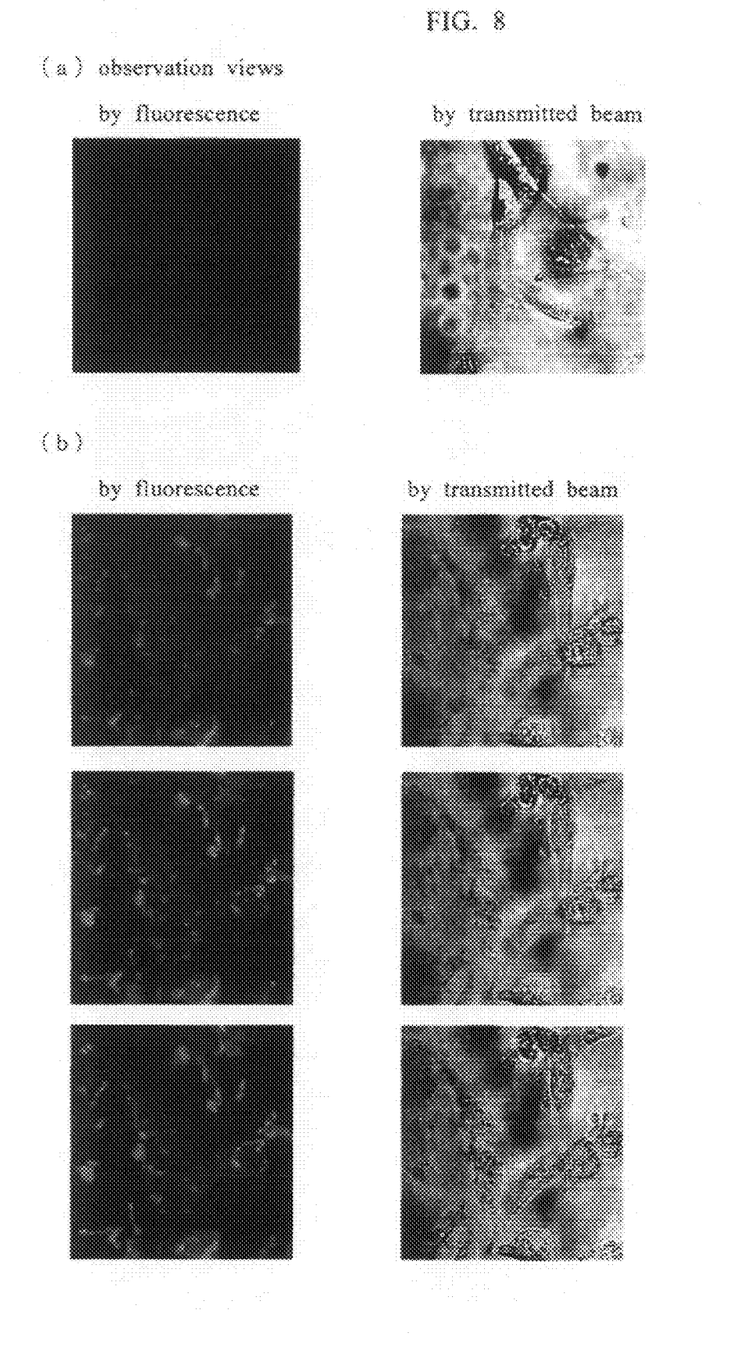
FIG. 8(a) is a group of views showing the accumulation of FITC-IgG conjugates in 3T3/SV40 cells, as observed by fluorescence (left) and transmitted beam (right).
FIG. 8(b) is a group of views showing the accumulation of FITC-IgG-PEI600 conjugates in 3T3/SV40 cells, as observed by fluorescence (left) and transmitted beam (right). The views were obtained by observing 0.5 μm cross sections of 3T3/SV40 cells under microscope.

3T3/SV40 cells were cultured in DMEM+10% FBS medium, FITC-IgG-PEI 600 conjugates were added to the culture supernatant, and after 12 hours the accumulation of conjugates in the cells were observed by fluorescence. For comparison, the same experiment was conducted using FITC-IgG conjugates which do not have PEI600 bound thereto. The observed results are shown in FIG. 8. As understood from the observed results in FIG. 8, although 50 µM of FITC-IgG conjugates was added, almost no FITC-IgG conjugates were accumulated in the cells (FIG. 8(*a*)). On the contrary, it is understood that FITC-IgG-PEI600 conjugates were efficiently accumulated in the cells (FIG. 8(*b*)). Further, 0.5 µm cross sections of cells were observed under microscope. Since fluorescence was observed from their cross sections, it was confirmed that the conjugates of the present invention were not merely superficially but internally accumulated in the cells. It is noted that fluorescence observation was conducted on living cells, so cell fixation or the like was not conducted.

EXAMPLE 7

Synthesis of IgG-PEI600 Conjugates

Human S100C protein (SWISS-PROT Accession Number P31949) is a protein that binds with intracellular actin filaments (Sakaguchi, M. et al., J. Cell boil. 149, 1193-1206 (2000)). Human S1000C prepared as recombinant proteins were used as antigen proteins for sensitization, and IgG(A) containing anti-human S1000C antibodies were prepared from the serum of a sensitized rabbit. As a control, antibody mixture (antibodies having no specific binding ability with S100C; IgG(B)) was also prepared from the serum of an antigen-unsensitized rabbit. Conjugate synthesis of IgG(A) and IgG(B) with PEI600 was conducted in the same manner as Example 1. The obtained IgG(A)-PEI600 conjugates and IgG(B)-PEI600 conjugates were labeled with FITC, thereby obtaining IgG(A)-PEI600-FITC conjugates and IgG(B)-PEI600-FITC conjugates.

Figure 9:
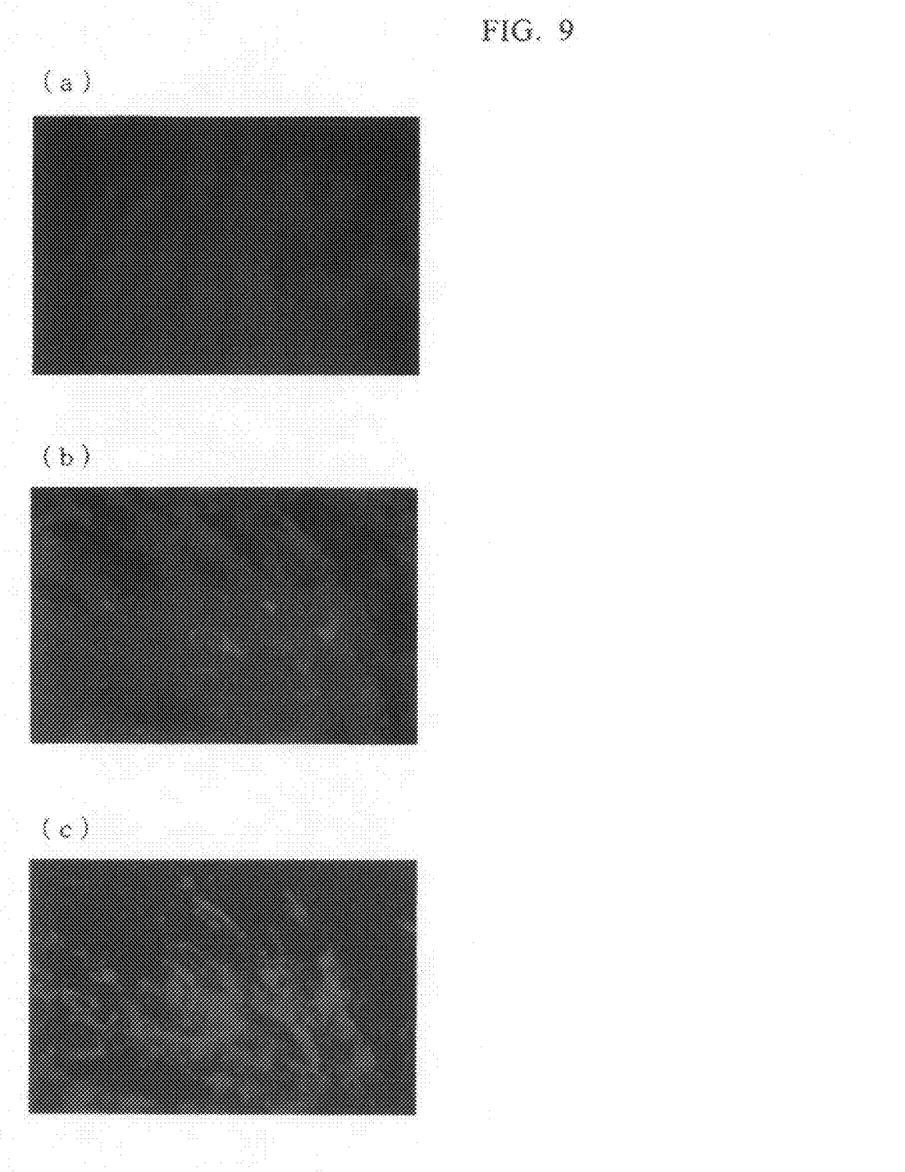
FIG. 9(a) is a view showing the accumulation of FITC-IgG (B)-PEI600 conjugates in KMS-6 cells, as observed by fluorescence.
FIG. 9(b) is a view showing the accumulation of FITC-IgG (A)-PEI600 conjugates in KMS-6 cells, as observed by fluorescence.
FIG. 9(c) is an observation view of actin filament-stained KMS-6 cells after FITC-IgG(A)-PEI600 was transduced therein.

Transduction of IgG-PEI600-FITC Conjugates into Cells and Evaluation of their Function Normal human fibroblast cells (KMS-6 cells) were cultured in DMEM+10% FBS medium, and separately added to the culture supernatant were IgG(A)-PEI600-FITC conjugates and IgG(B)-PEI600-FITC conjugates so as to have a concentration of 15 µg/ml, respectively. After 3 hours of cultivation at 37° C., the media were removed and replaced with fresh DMEM+10% FBS medium containing no samples (cationized antibodies), and they were cultivated for another 24 hours. Observations through a fluorescence microscope were made on the accumulation of different IgG-PEI600-FITC conjugates in the cells by. The observed results are shown in FIG. 9. When the antibody mixture, that is conjugates containing IgG(B), was used, fluorescence was observed over the whole cell (FIG. 9(*a*)). In contrast, when conjugates containing IgG(A) were used, the conjugates were localized (FIG. 9(*b*)). Moreover, cells having IgG(A) conjugates transduced thereinto were fixed, and thereafter these cells were stained with actin filaments using BODIPY 558/568-conjugated phalloidin (Molecular Probes Inc.). The results are shown in FIG. 9(*c*). According to the results, conjugates containing IgG(A) were co-localized with actin filaments. This indicates that IgG(A)-PEI600-FITC conjugates intracellularly recognize and specifically bind to S100C without the loss of the specific antibody ability against S100C of IgG(A).

EXAMPLE 8

Figure 10:
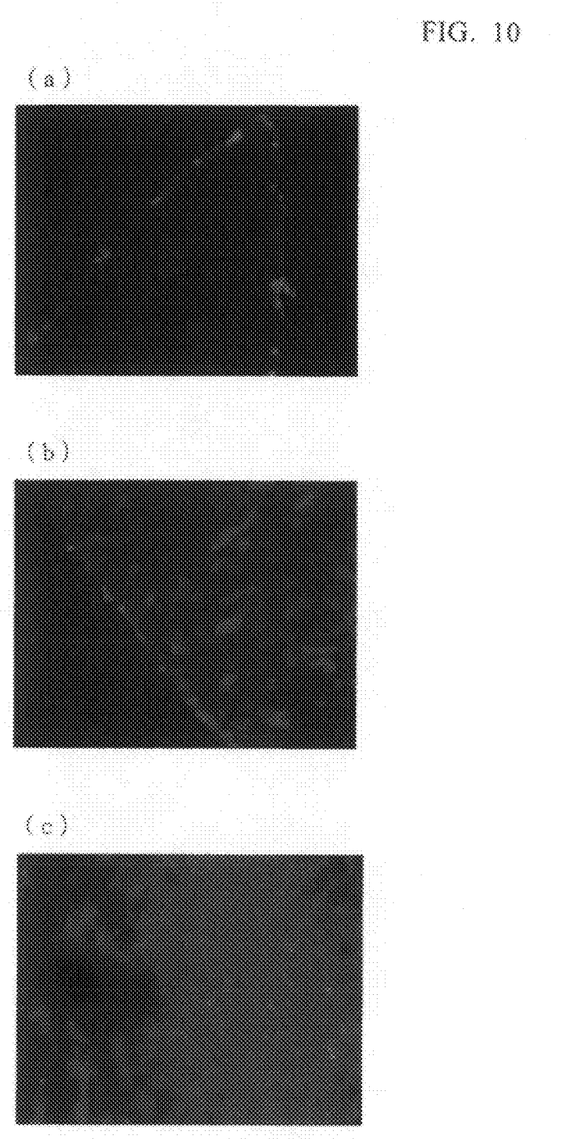
FIG. 10(a) is a view showing the accumulation of eGFP-PEI600 conjugates in mice livers, as observed by fluorescence.
FIG. 10(b) is a view showing the accumulation of eGFP-PEI600 conjugates in mice kidneys, as observed by fluorescence.
FIG. 10(c) is a view showing the accumulation of eGFP-PEI600 conjugates in rat livers by fluorescence.

Evaluation of the Accumulation of eGFP-PEI Conjugates which were Intraperitoneally Injected into Mouse Organs 300 μg of eGFP-PEI600 prepared in accordance with Example 2 and 300 μg of Native eGFP were respectively dissolved into physiological saline (0.9% NaCl), and each was intraperitoneally injected into C57BL/6 mice (8 weeks old). After 8 hours, the mice were autopsied, and their livers and kidneys were extirpated and subjected to quick freezing in Tissue-Tek (Miles Scientific, MA). 10 μm of frozen tissue sections were individually prepared using a cryostat, and observed by a fluorescence microscope for conjugate accumulation in the organs. According to the results (liver: FIG. 10(a), kidney; FIG. 10(b)), accumulation of eGFP-PEI600 was observed mainly on organ surfaces, and in addition, in the case of kidney, internal accumulation thereof was observed. In contrast, when Native eGFP was injected, its accumulation in the organs was not observed.

Evaluation of the Accumulation of eGFP-PEI600 Conjugates which were Intraportally Injected into Rat Liver Tissues 100 μg of eGFP-PEI600 prepared in accordance with Example 2 and 100 μg of Native eGFP were respectively dissolved into physiological saline (0.9% NaCl), and each was intraportally injected into anesthetized Wister rats (8 weeks old). After 1 hour, the livers were extirpated and subjected to quick freezing in Tissue-Tek (Miles Scientific, MA). 10 μm of frozen tissue sections were individually prepared using a cryostat, and observed by a fluorescence microscope for conjugate accumulation in the livers (FIG. 10(c)). According to the results, it was observed that eGFP-PEI600 was preferentially accumulated around the hepatic portal vein, and also there was a gradient transition of eGFP-PEI600 toward the central vein. On the other hand, when Native eGFP was injected, such a state was not observed.

EXAMPLE 9

Synthesis of Cataionic Polymers-RnaseA Conjugates

TABLE 2

| Polymer having cation value | Number average molecular weight (Mn) | Amine value (actual value) (mmol/g) | Cation value (amine value × Mn)/1000 |
|---|---|---|---|
| Hex-PEI600[1] | 800 | 13 | 10 |
| Dec-PEI600[2] | 1000 | 10 | 10 |
| Polyallylamine | 1000 | 15 | 15 |
| Polyallylamine | 3000 | 15 | 45 |
| Liner chain PEI7000[3] | 7000 | 20 | 140 |

[1] Compounds formed by introducing approximately 4 hexyl groups into PEI600
[2] Compounds formed by introducing approximately 5 decyl groups into PEI600
[3] Hydrolysates of products formed by ring-opening polymerization of methyl oxazoline Various cationic polymer-RNaseA conjugates were synthesized using RNaseA conjugates and polymers having various cation values as shown in Table 2. 10 mg of RNaseA was dissolved into 1.0 ml of 40 mg/ml cationic polymer aqueous solution (adjusted to pH 5 with hydrochloric acid), and then 3.0 mg of EDC was added thereto and the mixture was reacted for 4 hours at room temperature. After the reaction, the resultant solution was dialyzed against water, thereby obtaining cationic polymer-RNaseA conjugates.

Transduction of RNaseA-Cationic Polymer Conjugates into Cells

Figure 11:
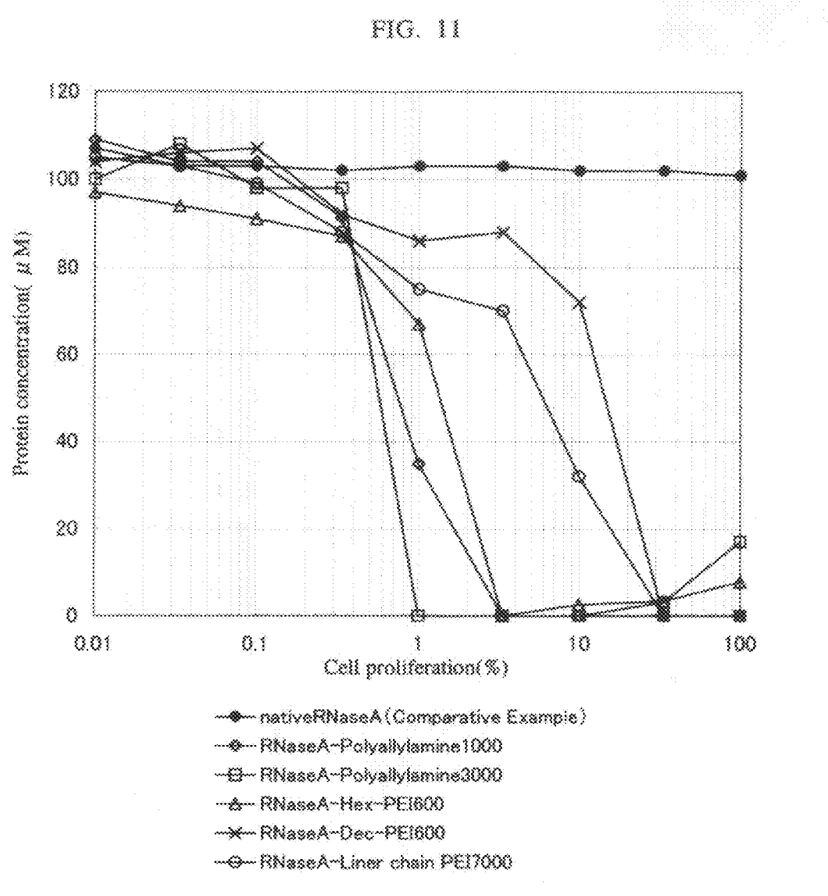
FIG. 11 is a graph showing the accumulation of RNaseA-cationized polymer conjugates of the present invention in 3T3/SV40 cells and inhibition of cell proliferation.

The above conjugates were each evaluated in terms of inhibition of 3T3/SV40 cell proliferation. The test for the inhibition of cell proliferation was conducted in the same manner as described in Example 1. The results are shown in FIG. 11. Native RNaseA was not accumulated in cells and significant inhibition of cell proliferation was not exhibited. However, when the conjugates of the present invention was used, inhibition of cell proliferation was exhibited, and further it was confirmed that the conjugates of the present invention were efficiently transduced into the cells.

INDUSTRIAL APPLICABILITY

According to the present invention, there is provided a method for transducing a protein into cells without serious loss of the protein function and with remarkably high efficiency and time and amount controllability.

Namely, the gene introduction method has conventionally been the mainstream method for enabling a designated protein to function in cells, and this method is suitable for constant expression and functioning in cells of the protein. In contrast, a method for transducing a protein into cells according to the present invention is suitable for transient functioning of the protein. This type of a novel technique can be a means for function analysis of a protein whose function is unknown. Furthermore, this technique can be a means for solving various problems with which the conventional gene introduction method is burdened.

Moreover, in comparison with the conventional method of cationization by ethylenediamine which requires modification of many side chains within a protein molecule, since the method of the present invention enables many cations to be introduced by modifying a small number of side chains i.e. within the range of one to several side chains, it exerts slight influence on the structure and function of the protein.

All the publications and patent applications cited herein are incorporated by reference in their entirety.

What is claimed is:

1. A method for transducing a protein or peptide pharmaceutical agent into a cell, comprising
    forming a conjugate by binding the pharmaceutical agent with a polymer which is chosen from polyalkylenepolyamines, polyallylamines, polyvinylamines, poly(dialkylaminoalkyl (meth)acrylate)s, poly(meth) acrylic dialkylaminoalkylamides, polyamidines, polyvinylpyridines, polyvinylimidazoles and co-polymers and salts thereof, and having a cation value of more than 2 and no more than 250 and
    then transducing the conjugate into the cell,
    wherein the pharmaceutical agent and polymer are either directly covalently bound without any intermediate therebetween, or are covalently bound by a bifunctional crosslinking reagent, and
    wherein the pharmaceutical agent is a fluorescently labeled protein or peptide.

2. The method of claim 1 wherein the polymer comprises polyalkylenepolyamine.

3. The method of claim 1 wherein the polymer comprises polyallylamine.

4. The method of claim 3 wherein the polyallylamine comprises polydiallyldimethylammonium chloride.

* * * * *